(12) United States Patent
Murphy et al.

(10) Patent No.: US 6,861,230 B1
(45) Date of Patent: Mar. 1, 2005

(54) ANTIBIOTIC SENSITIVITY TESTING

(75) Inventors: Melanie J Murphy, Salisbury (GB); Rachel L Price, Salisbury (GB); David J Squirrell, Salisbury (GB)

(73) Assignee: The Secretary of State for Defence in Her Britannic Majesty's Government of the United Kingdom of Great Britain and Northern Ireland, Hampshire (GB)

( * ) Notice: Subject to any disclaimer, the term of this patent is extended or adjusted under 35 U.S.C. 154(b) by 0 days.

(21) Appl. No.: 09/600,398
(22) PCT Filed: Jan. 12, 1999
(86) PCT No.: PCT/GB99/00089
§ 371 (c)(1), (2), (4) Date: Jul. 17, 2000
(87) PCT Pub. No.: WO99/37799
PCT Pub. Date: Jul. 29, 1999

(30) Foreign Application Priority Data

Jan. 21, 1998 (GB) .............................................. 9801126
Aug. 6, 1998 (GB) .............................................. 9816993

(51) Int. Cl.[7] ................... G01N 33/569; G01N 33/573; G01N 33/53; C12Q 1/02; C12Q 1/14
(52) U.S. Cl. ......................... 435/7.32; 424/9.1; 424/9.2; 435/7.4; 435/7.6; 435/7.91; 435/29; 435/36; 435/41; 435/69.2; 435/183; 435/243; 435/252.1; 435/259
(58) Field of Search ...................... 424/9.1, 9.2, 9.351, 424/85, 130.1, 144.1, 145.1; 435/7.32, 7.4, 7.6, 7.91, 29.36, 69.2, 183, 243, 252.1, 259, 7.24, 7.33, 7.8, 69.1, 69.3, 69.5

(56) References Cited

U.S. PATENT DOCUMENTS 3,933,592 A  1/1976  Clendenning ............ 195/103.5

FOREIGN PATENT DOCUMENTS

| EP | WO 94/06931 | * | 3/1994 | ............ C12Q/1/04 |
| GB | WO 96/02666 | * | 2/1996 | ............ C12Q/1/04 |
| WO | 94 06931 | | 3/1994 | |
| WO | 94 17202 A | | 4/1994 | |
| WO | 96 02665 A | | 1/1996 | |
| WO | 96 02666 A | | 1/1996 | |

OTHER PUBLICATIONS

Patent Abstracts of Japan vol. 017, No. 243 (C–1058), May 17, 1993 & JP 04 370100 A (Merician Corp), Dec. 22, 1992.

Squirrell, D.J. et al: "Andenylate kinase as a cell marker in bioluminescent assays" Biolumin. Chemilumin., Proc. Int. Symp., 8th (1994), 486–489. Editor(s): Campbell, Andrew Keith; Kricka, Larry J., Chichester, UK, Coden: 62UZAR, XP002102121 see the whole document.

Murphy, M. J. et al: "The use of adenylate kinase for the detection and identification of low numbers of microorganisms" Biolumin. Chemilumin., Proc. Int. Symp., 9th (1997), Meeting date 1996, 319–322. Editor(s): Hasting, J.W.;Kricka, L.J.; Stanley, P.E. Publisher: Wiley, Chichester, UK. Coden: 65JYAO, XP002102122 see the whole document.

Blasco, R. et al: "Specific assays for bacteria using phage mediated release of adenylate kinase" J. Appl. Microbiol. (1998), 84(4), 661–666 Coden: JMIFK; ISSN: 1364–5072, Apr. 1998, XP002102123 see whole document.

* cited by examiner

Primary Examiner—Lynette R. F. Smith
Assistant Examiner—J. Hines
(74) Attorney, Agent, or Firm—Nixon & Vanderhye P.C.

(57) ABSTRACT

The use of an assay for adenylate kinase in an in vitro test for the effect of external conditions on the growth characteristics of bacterial cells. Such tests in particular include tests for the sensivity of a bacteria to an antibiotic or a biostatic agent, and tests to assess the growth stage and health of the bacteria. Methods of carrying out these tests and kits for effecting them are also described and claimed.

18 Claims, 4 Drawing Sheets

Fig. 4.

Results from a test with a lytic antibiotic

SUSCEPTIBLE

| No additions | Plus antibiotic |
|---|---|
| − | + |

| Plus phage | Plus phage and antibiotic |
|---|---|
| + + | + |

RESISTANT

| No additions | Plus antibiotic |
|---|---|
| − | − |

| Plus phage | Plus phage and antibiotic |
|---|---|
| + + | + + |

Results from a test with a non-lytic antibiotic

SUSCEPTIBLE

| No additions | Plus antibiotic |
|---|---|
| − | − |

| Plus phage | Plus phage and antibiotic |
|---|---|
| + + | − |

RESISTANT

| No additions | Plus antibiotic |
|---|---|
| − | − |

| Plus phage | Plus phage and antibiotic |
|---|---|
| + + | + + |

―o― Sensitive E. coli 10243 with ampicillin and phage 10359
―∇― No lytic agents
―□― Resistant E. coli 10243 with ampicillin and phage 10359

ANTIBIOTIC SENSITIVITY TESTING

The present application is a 371 U.S. National Phase of Application No. PCT/GB99/00089, which designated the U.S., and was filed Jan. 12, 1999.

The present invention relates to a method for testing the growth characteristics of bacteria, in particular to testing for sensitivity to particular antibiotics or biostatic agents, as well as to kits for use in the method.

Bacteria with antibiotic resistance are becoming an increasingly serious problem. The current method for determining the antibiotic resistances of a strain of bacteria is very time consuming. It requires first the isolation of the organism in pure culture. A 'lawn' of the bacteria is then prepared and allowed to grow in the presence of a set of antibiotics. Zones of inhibition of growth around a particular antibiotic show that the bacteria are susceptible (with the size of the zone indicating the degree of susceptibility). Uninhibited growth in the presence of an antibiotic indicates resistance. The process takes at least two days to complete which is far from ideal, particularly in a clinical situation, where the optimum treatment regime of an infected individual may be determined as a result of these tests.

There is a need for a test which allows relatively rapid assessment of antibiotic resistance or susceptibility, for example within a few hours.

Assays for the detection of microorgansims by measurement of adenylate kinase are known for example from International Patent Application Nos. PCT/GB94/00118 and PCT/GB94/01513. Adenylate kinase is an essential enzyme in all living cells which, in the presence of ADP, catalyses the ATP producing reaction shown below.

$$2ADP \rightleftharpoons ATP + AMP$$

In this assay, ADP is added as a reagent to the sample under test, preferably in the presence of magnesium ions. ATP produced as a result of the above-mentioned adenylate kinase reaction can then be detected for example using firefly bioluminescence. For this, reagents such as the combination luciferin/luciferase are added to the mixture, generally after a short incubation period, for example of about 5 minutes, and the luminescent signal produced is monitored.

The sensitivity of this assay is limited only by the background level of adenylate kinase and the purity of reagents used. For example, using *E. coli* as a model system, the adenylate kinase activity from fewer than 100 cells was measured in a 5 minute incubation assay as illustrated in FIG. 1 hereinafter. In the tests used to generate this Figure, the sample volume was 200 μl.

The applicants have found that adenylate kinase can be used as a sensitive marker of biomass and that the above-mentioned assay techniques-can be utilised in studies which give much more detailed information regarding the growth characteristics of bacterial cells.

Thus the invention provides the use of an assay for adenylate kinase in an in vitro test for the effect of external conditions on the growth characteristics of bacterial cells.

The adenylate kinase assay provides a rapid and sensitive means of investigating many aspects of bacterial growth and inhibition. The sort of external conditions which may be investigated using the invention are various. For example, the adenylate kinase assay may be used in methods to determine the sensitivity of a particular bacterial strain or mixed culture to particular antibiotic or biostatic reagents, or the methods may be adapted for use in the screening of reagents for antibiotic or biostatic properties. It has also been found that a comparison of the extracellular adenylate kinase content of a cell culture with the total intracellular and extracellular content is indicative of the growth status and health of the cell culture and thus the adenylate kinase assay may be used to assess these features.

The configuration of the test will take into account the nature of the investigations being undertaken, the type of bacterial samples available, the nature of the samples any reagents if any, which are to be tested and in particular whether they have lytic or non-lytic effects on the cells. Various forms of these tests will be described in more detail hereinafter.

In particular however, the invention provides a method for determining the susceptibility of a bacteria to a test material, which method comprises assaying for the adenylate kinase released by lysis of bacteria from a culture containing said reagent and comparing the results with those obtained from a similar adenylate kinase assay which is either of the culture prior to addition of reagent, and/or of lysed bacteria from the same culture at a different point in time and/or of lysed bacteria from a similar culture which does not contain the reagent.

The reagents tested may be known antibiotics or biostatic agents, or they may be novel compounds or reagents not previously known as antibiotics so that the test forms part of a screening program.

Some reagents, e.g. antibiotics such as β-lactam antibiotics such as penicillins like ampicillin and amoxycillin, will cause lysis of bacteria in the culture. Where this does not occur however, it may be necessary to lyse the bacteria prior to effecting the assay. This may be done by various techniques as understood in the art, including treatment with lytic agents as well as physical methods such as subjecting the bacteria to magnetic or electrical fields, or sonication.

Agents producing lysis of bacteria include detergents and enzymes such as bacteriolysin. These are non-specific however and will liberate AK from all living material present in the sample. This may be suitable where the sample comprises a pure culture. However, where the bacteria under investigation is a component of a mixed culture, other strategies may be adopted. Specific measurements from target cells in a mixed sample may be achieved for example by: 1) specific capture of the cells of interest to separate them from contaminating organisms followed by non-specific adenylate kinase measurements; 2) use of a method which only lyses the target cells so only the adenylate kinase from these is measured; or 3) a combination thereof.

Adenylate kinase from the target bacterial cells only (2 above) may be liberated by using a lytic agent which is specific for the particular bacteria under investigation, for example a bacteriophage which is specific for the target bacteria and which brings about lysis of that bacteria. These bacteriophages are viruses which infect bacteria, causing lysis of the cells and release of intracellular components, including adenylate kinase, into the external medium. This release generally occurs about 30 to 60 minutes after infection. It has been found that fewer than 500 cells are detectable using this method in an assay taking 40 minutes.

Phages can infect target cells equally well in pure or mixed culture. By comparing the amount of adenylate kinase which can be chemically extracted from a sample with the amount released after a set time with phage infection, the presence or absence of target cells can be determined and the effects of the test material on their growth measured.

In order for bacteriophage to reproduce and therefore bring about lysis, the host cell must be in the log phase of growth. If growth is inhibited for example, as a result of the presence of a bacteriostatic agent or antibiotic, the bacteriophage will not be able to grow and lyse the cells. This can be used as a basis for a further embodiment of the invention as illustrated below.

Alternatively or additionally, a mixed culture may be subjected to a pretreatment step wherein the target bacterial cells are either enriched in the culture and/or separated from it. Such steps are well known in the art. For example, separation may be effected using immunocapture techniques where antibodies or binding fragments thereof which are specific for particular bacteria are used to immobilise those cells on a solid surface, such as a beads, microtitre plates, filter membranes or columns. Magnetic beads may provide a particularly preferred solid surface. Separation of the beads, where appropriate using magnetic separation techniques leads to substantial isolation of the target bacteria as illustrated hereinafter. It has been found that typically, using magnetic beads as the solid support, detection of fewer than 1000 cells can be achieved with a total assay time of about 30 min. Other materials may also be used as a solid support.

Further specificity may be gained by the use of selective growth media. This can be used in the enrichment step to establish a healthy growing culture, either prior to the immunocapture assay, or infection by a bacteriophage. Additionally, selective media can be used throughout the course of the bacteriophage infection.

Such media will minimise overgrowth by non-target organisms, which may be present, sometimes vastly in excess of the target bacteria.

As mentioned above, the invention may be adapted for use in the testing of bacteria for susceptibility to particular antibiotics or bacteriostatic agents.

Antibiotics such as P-lactams like penicillins work by disrupting cell wall synthesis thereby causing the cells to lose integrity and lyse during replication. This occurs relatively rapidly, about 10–15 minutes after exposure to the antibiotic, provided that the bacteria are actively growing.

Other antibiotics, such as chloramphenicol, do not cause cell lysis but inhibit cell growth in other ways, as do biostatic agents. The mode of action of any particular agent in use is generally understood. The invention may be adapted for use in testing the sensitivity to bacteria to any of these agents.

Specific embodiments of the invention include a method for determining the sensitivity of a bacteria to a lytic antibiotic, said method comprising the steps of (i) separating said bacteria from other microbial species, for example using an immunocapture step; (ii) determining the extracellular adenylate kinase content of a culture of said bacteria (iii) adding the lytic antibiotic to the culture and incubating it for a period sufficient to allow the antibiotic to exert its lytic effect, and (iv) determining the extracellular adenylate kinase content of the culture to assess whether lysis has taken place.

In this test, sensitive bacteria would be lysed by the antibiotic soon after addition thereof, generally within about 15 minutes. Hence the free adenylate kinase content of the culture would increase significantly following addition of the antibiotic as the bacterial cells break open liberating intracellular adenylate kinase. Optimally measurement of the adenylate kinase levels would be taken shortly before antibiotic addition, and then again at least 15 minutes after antibiotic addition. The free adenylate kinase content of cultures of resistant bacteria would remain largely constant. Only the normally present, low level extracellular adenylate kinase content would therefore be measured and, as explained above, this remains approximately steady for healthy growing cells. Using this method, an assessment of antibiotic sensitivity may be achieved in a period of approximately 40 minutes.

The culture of bacteria used in this method may comprise a selective growth medium which favours said bacteria as discussed above as this will minimise any false positive results as a result of contamination.

Alternatively another embodiment of the invention provides a method for determining the sensitivity of a bacteria to a non-lytic antibiotic or biostatic agent, said method comprising (i) separating said bacteria from other microbial species, for example using an immunocapture technique, (ii) incubating a culture of said bacteria in the presence of said non-lytic antibiotic or biostatic agent and optionally a selective growth medium which favours said bacteria, (iii) determining whether the total adenylate kinase content of the culture increases or decreases over the period of the incubation by removing samples at spaced time periods, lysing bacteria in these samples and assaying for adenylate kinase in said samples.

In this case, the amount of adenylate kinase obtainable following chemical lysis over a period of time, for example of about an hour, will remain approximately constant if the bacteria are susceptible to the antibiotic. This is because the bacteria are not able to grow in the presence of the antibiotic. In the case of resistant bacteria however, they will continue to grow and so the levels of adenylate kinase will increase steadily with time.

Thus, the sensitivity of a pure culture to any particular antibiotic, whether lytic or non-lytic, may be determined rapidly using the methodology of step I above.

Other embodiments of the invention avoid the need for using isolated or pure cultures of bacteria. In particular the invention further provides a method for determining the sensisitivity of a bacteria to an antibiotic or biostatic agent, said method comprising (a) incubating a first sample of a culture of said bacteria, a second sample in the presence of said antibiotic, a third sample in the presence of a bacteriophage which will specifically lyse said target bacteria and a fourth sample in the presence of both said bacteriophage and said antibiotic;

(b) determining the adenylate kinase content of each of the first to fourth samples after culture, and (c) determining the sensitivity or resistivity of the bacteria on the basis of the adenylate kinase assay results and on the mode of action of the antibiotic or biostatic agent.

Since bacteria must be actively growing in order to be suceptible to antibiotic effect, selective media could be used for an initial enrichment step. This may comprise an incubation of about an hour. After this time the target cells may, if desired, be concentrated by immunocapture into fresh selective medium. The effect of adding antibiotics to the target cells could be determined using adenylate kinase measurements in combination with bacteriophage mediated lysis.

In order for a bacteriophage to reproduce, the host cell must be in the log phase of growth. If growth is inhibited, e.g. due to the presence of an antibiotic, then the phage will not be able to replicate and will, therefore, not be able to cause the host cells to be lysed. Using the adenylate kinase assay in conjunction with bacteriophage, the antibiotic sensitivities of bacteria can be determined within 3 hours.

The additional time is needed to establish healthy, growing cells prior to exposure to the antibiotic or infection by the phage. Two types of test outcome are possible depending upon the mode of action of the antibiotic concerned.

The results obtained are summarised in FIG. 4 where indicates a result which is consistent with the detection of extracellular adenylate kinase only, "+" indicates a moderately positive result consistent with the detection of intra and extracellular adenylate kinase of the existing sample with no growth, and "++" a indicates the detection of elevated levels of adenylate kinase consistent with lysis of the growing culture.

As is clear from FIG. 4, the pattern of the results obtained using this series of tests can allow ready distinction between susceptible and resistant bacteria, provided the mode of action (lytic or non-lytic) of the agent is understood. The different effects are created as a result of the interaction of the various reagents with the bacteria as will be explained in more detail in the Examples given below.

It has been found that a comparison of the extracellular adenylate kinase content of a cell culture with the total intracellular and extracellular content is indicative of the growth status and health of the cell culture.

Therefore, yet a further embodiment of the invention provides a method of determining the growth phase of a bacterial culture which method comprises
(a) subjecting a first sample of said bacterial culture to a lytic reagent so as to lyse bacterial cells therein;
(b) assaying for adenylate kinase in said first sample and also in a second sample of said culture which has not been exposed to the lytic agent; and
(c) comparing the results obtained from said first and second cultures and assessing the growth stage of the culture.

Healthy, log phase cultures have relatively low extracellular adenylate kinase levels (about 1% of the total adenylate kinase) and that the proportion of extracellular adenylate kinase stays relatively constant throughout log phase, and increases as the culture approaches stationary phase. Stationary phase cultures may have as much as a third of the total adenylate kinase in the culture medium. Therefore, using adenylate kinase, the health of cells, as well as their number can be rapidly determined.

This method can be used to, for example to confirm that a particular cell culture is growing well, for example where optimum growth is required, for example in fermentation or other processes where bacterial products are required. Alternatively, it may be necessary to confirm cells are growing strongly when screening for antibiotic or bacteriostatic compounds so that false postive results are avoided because weak or stationary phase cultures being used in the test. Furthermore, it may be used to determine what effect environmental factors, such as temperature or culture media, have on the growth of any particular culture.

In each case, the adenylate kinase content may be assessed by removing samples of the culture and carrying out an adenylate kinase assay for example as described in International Patent Application Nos. PCT/GB94/00118 and PCT/GB94/01513.

The invention also provides test kits for effecting the methods of the invention. The test kit will contain suitable components which would allow the particular assay to be carried out. For example, for antibiotic sensitivity testing kits may comprise a range of antibiotics, for example in freeze-dried or other preserved states. It may also comprise reagents for extracting adenylate kinase from a sample such as detergents or other chemical lytic agents as well as reagents necessary for assaying for adenylate kinase, such as luciferin/luciferase etc. In addition, for use in situations where mixed bacterial cultures are to be tested, the kits may contain suitable bacteriophages, also in preserved states such as freeze-dried bacteriophages. Additionally, the kits may comprises suitable selective growth media. The reagents may be supplied in a suitable reaction container such as a multi-well plate.

The invention will now be particularly described by way of example with reference to the accompanying diagrammatic drawings in which:

FIG. 1 is a graph showing the results of experiments to measure the adenylate kinase activity from $E.$ $coli$ cells;

FIG. 2: shows the results of magnetic bead immunocapture assays for $Salmonella$ $typhimurium$ in a pure culture and in the presence of $3.5 \times 10^5$ $Bacillus$ $ubtilis$ var $niger$ vegetative cells; where ■ shows adenylate kinase activity from cells captured by beads; and □ shows adenylate kinase activity from residual cells in sample (i.e. in the left hand graph from uncaptured $Salmonella$ cells and in the right hand graph from these plus non-specific cells;

FIG. 4 is a summary diagram of antibiotic test results obtainable using an embodiment of the invention;

Figure 6:
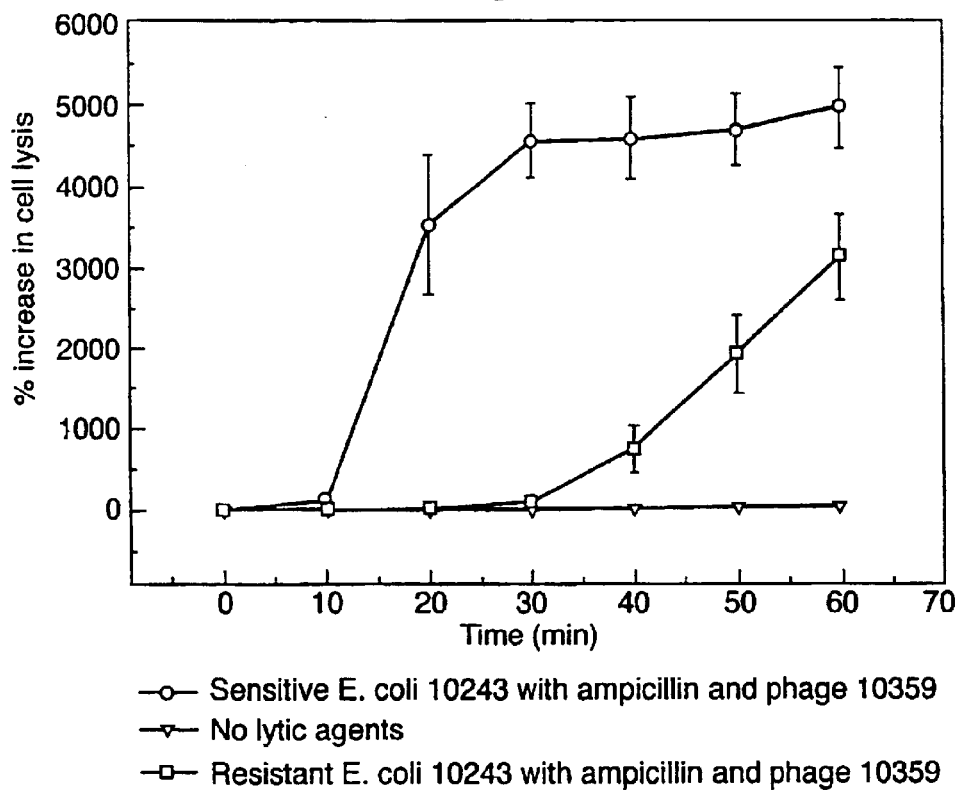
Figure 7:
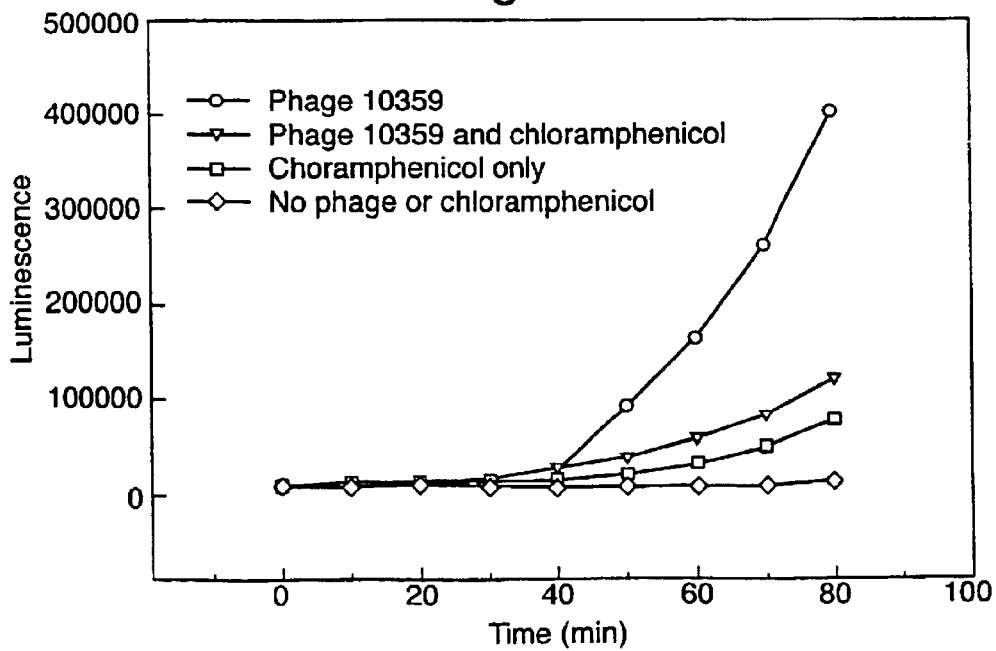

FIG. 6 shows the effect of Phage 10359 and 50 mg/liter ampicillin with ampicillin-sensitive and resistant cultures of $E.$ $coli$ 10243, in which 0 represents the results with sensitive $E.$ $coli$ 10243 with ampicillin and phage 10359, ▽ represents the results with no lytic agents and □ represents the results with resistant $E.$ $coli$ 10243 with ampillicin and phage; and FIG. 7 shows the effect of chloramphenical (34 mg/liter) and phage 10359 on cultures of $E.$ $coli$ 10243, in which 0 represents phage only, ▽ represents phage 10359 and chloramphenicol, □ represents chloramphenicol alone and 0 represents no phage or chloramphenicol.

EXAMPLE 1

Comparison of Extracellular and Total Adenylate Kinase Contents of a Culture

For example, in one embodiment, a sample of bacterial cells is divided into first and second samples. The first sample of bacterial cells is mixed with a solution containing ADP and a detergent in the presence of magnesium ions. This extracts the adenylate kinase from all the cells present in the sample, thus allowing the ATP generating reaction to occur. The reaction is allowed to proceed for the required time e.g. 5 minutes, after which bioluminescence reagent is added and the resulting light measured in a luminometer. An assay performed in this way determines the total amount of adenylate kinase in a sample, be it extracellular or intracellular.

The second sample is subjected to a similar assay but in the absence of detergent so that only extracellular adenylate kinase is measured.

EXAMPLE 2

Use of Immunocapture to Separate Target Cells from a Mixed Suspension

An immunocapture assay for $Salmonella$ $typhimurium$ from a pure go sample and from a sample also containing $3.5 \times 10^5$ $Bacillus$ $subtilis$ var $niger$ (BG) vegetative cells was carried out. Immunocapture assay carried out in a total volume of 300 $\mu$l. The immunocapture step, onto magnetic microbeads coated with $S.$ $typhimurium$ specific antibody, took 10 minutes. The immobilised beads were washed to remove unbound particles, and a non-specific lysis step was carried out to release adenylate kinase from bound material. This was detected using a 5 minute adenylate kinase assay.

Figure 1:
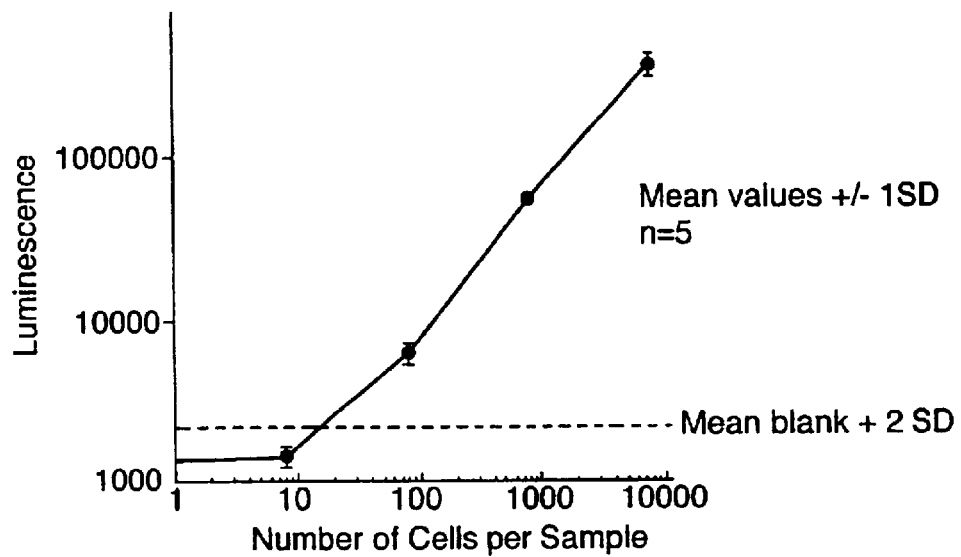
Figure 2:
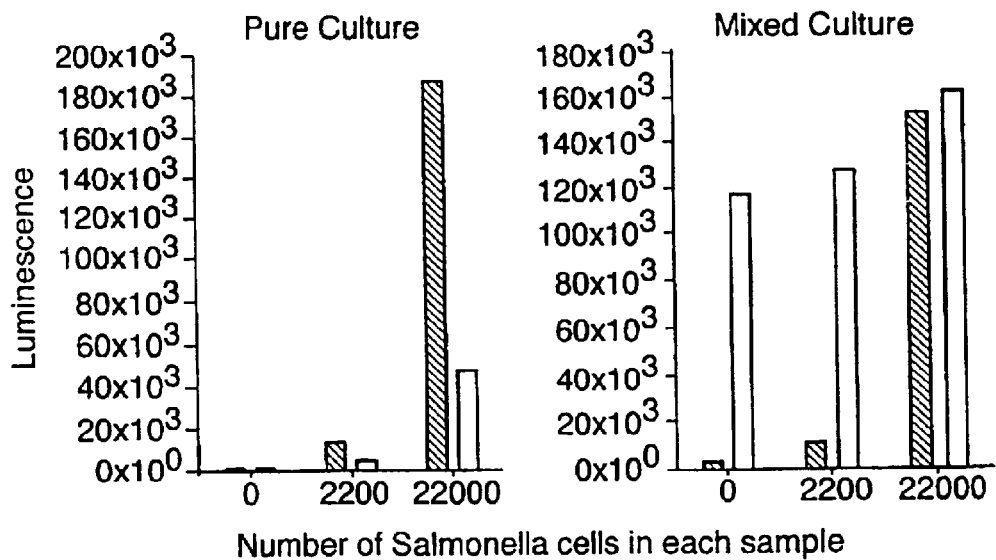

The results are shown in FIG. 2. The graphs show that about 70% of the target cells can be selectively removed from suspension, and that this is largely unaffected by the presence of contaminating material (the BG cells).

EXAMPLE 3
Use of Phage Mediated Lysis

Figure 3:
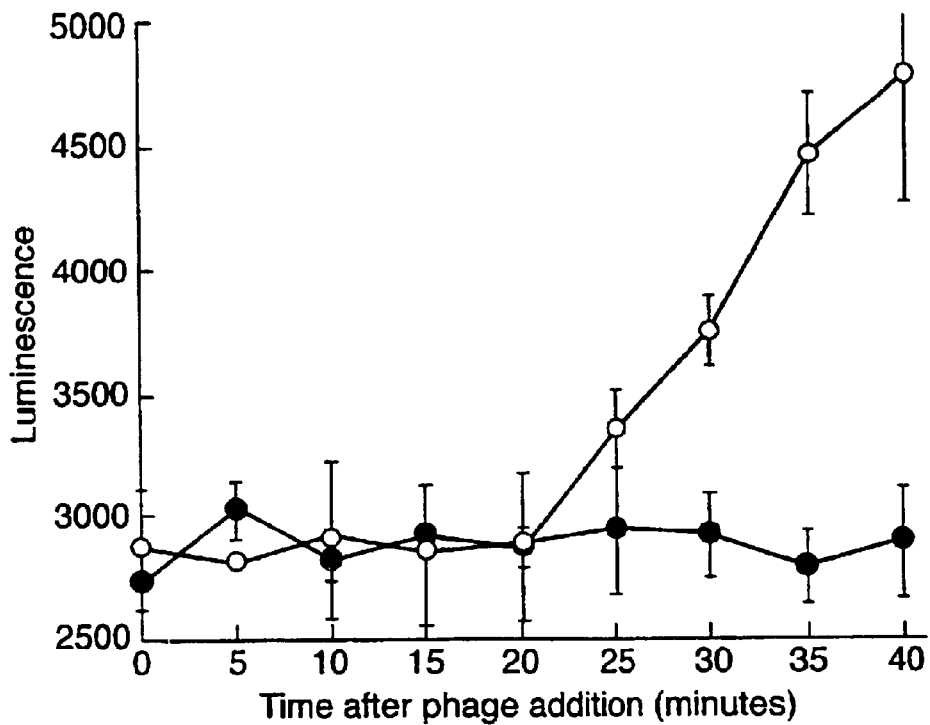
FIG. 3 is a graph showing results from an experiment to investigate the time course of phage mediated release of adenylate kinase from a culture of $Escherichia$ $coli$ cells.

The time course of adenylate kinase release from a culture of *Escherichia coli* cells, some of which were infected with *E. coli* specific bacteriophage was studied. 100 µl samples (each containing just 350 cells) were removed at timed intervals from a culture that had been infected with an *E. coli* specific bacteriophage and then assayed for extracellular adenylate kinase activity after 40 minutes. The results are shown in FIG. 3 where ○=infected culture, and ● non-infected control.

It is clear from these results that fewer than 500 cells are detectable using this method.

EXAMPLE 4
Antibiotic Sensitivity Assays:-Lytic Antibiotic

Sample cells (which may be mixed or pure cultures) are split into 2 fractions and one infected with bacteriophage. Each of these fractions is then further split into 2 fractions with one being exposed to antibiotic and the other left untreated. The relative levels of extracellular adenylate kinase produced in a set time shows the effects of both the antibiotic and bacteriophage on the target cells. Test results achieved in practise are illustrated in Table 1.

The results show both the antibiotic resistance state of the cells and controls to ensure that the test has functioned correctly.

TABLE 1

| Susceptible Bacteria | |
|---|---|
| (1) No antibiotic, no phage Low extracellular adenylate kinase levels only, (no lysis). | (2) Antibiotic, no phage adenylate kinase released through lysis due to antibiotic. |
| (3) No antibiotic, plus phage adenylate kinase released though lysis caused by phage. | (4) Antibiotic plus phage adenylate kinase released though lysis due to antibiotic and phage. Levels lower than (3) because of reduced cell growth and inhibition of phage replication. |
| Resistant Bacteria | |
| (1) No antibiotic, no phage Low extracellular adenylate kinase levels only (no lysis). | (2) Antibiotic, no phage Low extracellular adenylate kinase levels only, (no lysis). Same as (1). |
| (3) No antibiotic, plus phage adenylate kinase released lysis caused by phage. | (4) Antibiotic plus phage adenylate kinase released through lysis due to phage. Same as (3). |

EXAMPLE 5
Antibiotic Sensitivity Assays:-Non-Lytic Antibiotic or Biostatic Agent The susceptibility of bacteria to antibiotics which do not cause cell lysis, but inhibit cell growth in other ways, (and other chemicals which inhibit bacterial cell growth, such as biostatic agents) can also be rapidly determined using a similar method.

Sensitivity testing of bacteria in mixed culture to non-lytic antibiotics would be carried out in the same way as testing for susceptibility to antibiotics causing lysis. However, since the bacteria must be actively growing to permit bacteriophage infection, susceptibility to antibiotic would be indicated by a lack of phage mediated lysis in the treated sample.

The results which would be observed are summarised in Table 2.

TABLE 2

| Susceptible Bacteria | |
|---|---|
| (1) No antibiotic, no phage Low extracellular adenylate kinase levels only, (no lysis). | (2) Antibiotic, no phage Low extracellular adenylate kinase levels only, (no lysis). May be even lower than (1) through inhibition of growth. |
| (3) No antibiotic, plus adenylate kinase released through lysis caused by phage. | (4) Antibiotic plus phage Low extracellular adenylate kinase levels only, (no lysis). May be even lower than (1) through inhibition of growth. |
| Resistant Bacteria | |
| (1) No antibiotic, no phage Low extracellular adenylate kinase levels only, (no lysis). | (2) Antibiotic, no phage Low extracellular adenylate kinase levels only, (no lysis). Same as (1). |
| (3) No antibiotic, plus phage adenylate kinase released through lysis caused by phage. | (4) Antibiotic plus phage adenylate kinase released through lysis due to phage. Same as (3). |

EXAMPLE 6
Test Kit for Testing for Antibiotic Resistance

Figure 5:
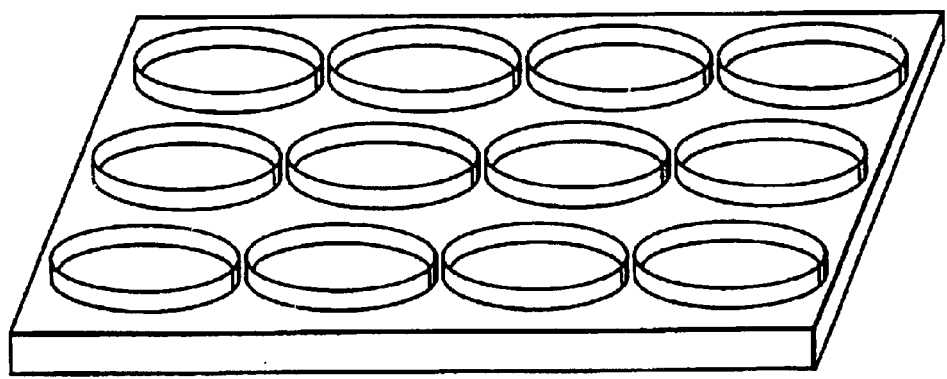
FIG. 5 is a diagram showing an assay plate for testing bacterial samples for antibiotic resistance.

A suitable test kit comprises a sample container which typically might be a plastic plate in which are formed a number of wells as illustrated in FIG. 5. The total volume of liquid that could be held in each well may be approximately 0.5 ml. The plates are suitably pre-prepared so that particular wells would contian appropriate freeze-dried (or otherwise preserved) preparations of antibiotics and/or bacteriophages, and optionally also selective growth media.

In a plate such as shown in FIG. 5, each row of 4 wells is designed to be used to test for resistance to a particular antibiotic, so using this plate, 3 antibiotics could be tested simultaneously.

In use, about 0.2 ml volume of the samples for test, which may be pure cultures, preparations enriched by immunocapture, samples from selective media or neat samples as appropriate, are added to each well. After incubation at, for example 37° C. for 1 hour, reagents to measure the adenylate kinase activity, may be added. These may be reagents which produce a colorimetric signal in the presence of adenylate kinase, or more preferably, reagents which generate a bioluminescence signal.

In particular ADP and a source of magnesium ions, followed after 5 minutes by luciferin and luciferase, would be added. The light emission would either be determined 1 well at a time by transfer to tubes and measurement in a tube luminometer, or, preferably, the plate would be assayed automatically in a plate luminometer or be imaged as a whole using a CCD camera system.

EXAMPLE 7
Comparison of the Effect of Lytic and Non-Lytic Antibiotics on Culture Growth The effect of lytic (ampicillin) and non-lytic (chloramphenicol) antibiotics on *E. coli* culture growth were examined.

A plasmid encoding ampicillin resistance (pUC18) was introduced into a pure culture of *E. coli* 10243 in order to induce resistance without altering phage host specificity. The resistant strain was also tested to ensure that carrying the plasmid did not alter its growth rate or infection by phage 10359, and was seen to be the same as the sensitive strain regarding growth and infection.

The adenylate kinase released from sensitive (untransformed) bacteria and resistant bacteria in the presence of the *E. coli* bacteriophage 10359 and either a lytic (ampicillin) or non-lytic (chloramphenicol) antibiotic were compared.

Log phase cultures of both resistant and sensitive strains of *E. coli* 10243 were infected with $10^5$ phage 10359 at $T_0$ and 50 µg/ml ampicillin at $T_5$. Cell lysis due to ampicillin was evident at $T_{10}$ and significant at $T_{20}$ in the sensitive strain, masking any tytic effects due to bacteriophage. The resistant strain was unaffected by the antibiotic but showed lysis due to phage infection after 20 minutes, although this was not significant unit $T_{40}$. The results are shown in FIG. 6. This shows that after only 40 min incubation in the presence of ampicillin and phage, the susceptibility of a culture of *E. coli* 10243 towards ampicillin can be determined.

Log phase cultures of *E. coli* 10243 were incubated in the presence of phage 10359 and/or chloramphenicol (34 µg/ml) over a period of 80 min and assayed for adenylate kinase as before. The results are shown in FIG. 7.

Greater cell lysis was demonstrated where cultures were incubated with both bacteriophage and chloramphenicol compared with chloramphenicol alone. Although chloramphenicol is not a lytic antibiotic, cells lysis were exhibited over the course of the incubation, probably due to cell death. The degree of phage mediated lysis was considerably less in cultures containing the antibiotic, because the bacteria were not growing well and thus prevented the phage from completing their replication cycle.

Following the results obtained with the ampicillin resistant mutant, it would be expected that a chloramphenicol resistant mutant would behave the same in both the presence and absence of the antibiotic. Therefore, after a 60 min incubation, the degree of increase in background luminescence would indicate whether or not a culture was susceptible to chloramphenicol.

What is claimed is:

1. A method for determining the susceptibility of a bacteria to a reagent selected from an antibiotic agent or a biostatic agent or a compound suspected of having an antibiotic property or a compound suspected of having a biostatic property, said method comprising the steps of:
    (i) dividing a culture comprising said bacteria into at least a first sample and a second sample;
    (ii) incubating said first sample in the presence of said reagent to form a first incubated sample, lysing bacteria in said first incubated sample to form a first lysed-incubated sample, exposing the first lysed-incubated sample to ADP, a source of magnesium ions, luciferin and luciferase, to form a first mixture, and measuring luminescence emitted from said first mixture as an indication of the amount of any adenylate kinase present in the first lysed-incubated sample;
    (iii) subjecting said second sample to either of the following steps (iii)(a) and (iii)(b);
        (a) incubating said second sample in the absence of said reagent to form a second incubated sample, lysing bacteria in said second incubated sample to form a second lysed-incubated sample, exposing the second lysed-incubated sample to ADP, a source of magnesium ions, luciferin and luciferase, to form a second mixture, and measuring luminescence emitted from said second mixture as an indication of the amount of any adenylate kinase present in the second lysed-incubated sample;
        (b) lysing bacteria in said second sample without further incubating said second sample, in the absence of said reagent, to form a first lysed sample, exposing the first lysed sample to ADP, a source of magnesium ions, luciferin and luciferase, to form a third mixture, and measuring luminescence emitted from said third mixture as an indication of the amount of any adenylate kinase present in the first lysed sample; and
    (iv) comparing the indicated amount of adenylate kinase present in the first lysed-incubated sample with the indicated amount of any adenylate kinase present in the second lysed-incubated sample or the first lysed sample as a determination of the susceptibility of said bacteria to the reagent, wherein
        (a) said bacteria are susceptible to said reagent when the indicated amount of adenylate kinase in said second lysed-incubated sample is greater than the indicated amount of adenylate kinase in said first lysed-incubated sample, the magnitude of the difference between said indicated amounts being indicative of the degree of susceptibility of said bacteria to said reagent, wherein a greater difference is indicative of a greater susceptibility, and
        (b) when the magnitude of the difference between the indicated amount of adenylate kinase in said first lysed-incubated sample is greater than the indicated amount of adenylate kinase in said first lysed sample, then the magnitude of the difference indicates the degree of susceptibility of said bacteria to said reagent, wherein a smaller difference is indicative of a greater susceptibility.

2. The method according to claim 1 wherein:
    said dividing step (i) further comprises dividing said culture in to a third sample; and
        said subjecting of step (iii) further comprises subjecting said third sample to step (iii)(a) to form a third lysed-incubated sample and an indicated amount of adenylate kinase present in the third lysed-incubated sample, if said second sample is subjected to step (iii)(b), or
        said subjecting of step (iii) further comprises subjecting said third sample to step (iii)(b) to form a second lysed sample and an indicated amount of adenylate kinase present in the second lysed sample, if said second sample is subjected to step (iii)(a); and
    comparing the indicated amount of any adenylate kinase present in step (ii) with the indicated amount of any adenylate kinase present in said third lysed-incubated sample or said second lysed sample to determine the susceptibility of said bacteria to the reagent, wherein
    the bacteria are susceptible to said reagent if the indicated amount of adenylate kinase present in said third lysed-incubated sample is greater than the indicated amount of adenylate kinase present in the first lysed-incubated sample, the magnitude of the difference between said indicated amounts being indicative of the degree of susceptibility of said bacteria to said reagent, wherein a greater difference is indicative of a greater susceptibility, and,
    when the magnitude of the difference between the indicated amount of adenylate kinase in said second lysed-incubated sample is greater than the indicated amount of adenylate kinase in said first lysed sample, then the magnitude of the difference indicates the degree of susceptibility of said bacteria to said reagent, wherein a smaller difference is indicative of a greater susceptibility.

3. The method according to claim 1 wherein bacteria are lysed using a chemical lytic agent.

4. The method according to claim 1 wherein the lytic agent is specific for a particular bacteria.

5. The method according to claim 4 wherein the lytic agent is a bacteriophage which infects and lyses a specific bacterial genus, species or strain.

6. The method according to claim 1 wherein bacteria are lysed using an enzyme.

7. The method according to claim 6, wherein the enzyme is bacteriolysin.

8. The method according to claim 1 wherein said culture is a mixed culture of bacteria, said mixed culture of bacteria comprising target bacteria and non-target bacteria and wherein the mixed culture of bacteria is first subjected to a separation step to substantially remove any non-target bacteria from the mixed culture.

9. The method according to claim 8 wherein the separation comprises an immunocapture technique.

10. The method according to claim 9 wherein target bacteria are concentrated at a solid surface on which antibodies or binding fragments thereof which are specific for the target bacteria are immobilized.

11. The method according to claim 1 wherein the culture further comprises a growth medium which selectively favors the bacteria.

12. A method for determining the susceptibility of a target bacteria to a lytic antibiotic, said method comprising the steps of (i) separating said target bacteria from any other microbial species, if present, (ii) determining the extracellular adenylate kinase content of a culture of said target bacteria, (iii) adding the lytic antibiotic to the culture to form a mixture and incubating said mixture for a period sufficient to allow the antibiotic to exert a lytic effect, and (iv) determining the extracellular adenylate kinase content of the incubated mixture to assess whether lysis has taken place, wherein a greater amount of extracellular adenylate kinase in step (iv) as compared with step (ii) indicates said bacteria is sensitive to the lytic antibiotic.

13. The method according to claim 12 wherein in step (i), the target bacteria are separated using immunocapture techniques.

14. The method according to claim 12 wherein the culture of target bacteria comprises a selective growth medium which favors said bacteria.

15. A method for determining the susceptibility of a target bacteria to a non-lytic antibiotic agent or a non-lytic biostatic agent, said method comprising (i) separating said target bacteria from other microbial species, if present, (ii) incubating a culture of said target bacteria in the presence of said non-lytic antibiotic agent or said non-lytic biostatic agent, (iii) determining whether the total adenylate kinase content of the culture increases or decreases over the period of the incubation by removing multiple samples at spaced time periods, lysing bacteria in said multiple samples and assaying for adenylate kinase in said multiple samples, wherein an increase in the amount of total adenylate kinase in said multiple samples over time indicates that said bacteria are not sensitive to said agent.

16. The method according to claim 15 wherein the bacteria are lysed using a chemical lytic agent.

17. The method according to claim 15 wherein in step (i), the target bacteria are separated using immunocapture techniques.

18. The method according to claim 15 wherein the culture of target bacteria comprises a selective growth medium which favors said bacteria.

* * * * *